(12) United States Patent
Danilovski et al.

(10) Patent No.: US 8,138,349 B2
(45) Date of Patent: Mar. 20, 2012

(54) PHARMACEUTICALLY ACCEPTABLE SALT AND POLYMORPHIC FORMS OF FLUPIRTINE MALEATE

(75) Inventors: Aleksandar Danilovski, Rijeka (HR); Maja Devčić, Zagreb (HR); Marina Marinković, Sesvete (HR); Ernest Meštrović, Bjelovar (HR); Tina Mundorfer, Zagreb (HR); Iva Tunjić, Zagreb (HR)

(73) Assignee: Pliva Hrvatska D.O.O., Zagreb (HR)

( * ) Notice: Subject to any disclaimer, the term of this patent is extended or adjusted under 35 U.S.C. 154(b) by 67 days.

(21) Appl. No.: 12/309,260

(22) PCT Filed: Jul. 13, 2007

(86) PCT No.: PCT/GB2007/002647
§ 371 (c)(1),
(2), (4) Date: Mar. 25, 2011

(87) PCT Pub. No.: WO2008/007117
PCT Pub. Date: Jan. 17, 2008

(65) Prior Publication Data
US 2011/0184030 A1    Jul. 28, 2011

(30) Foreign Application Priority Data
Jul. 13, 2006  (GB) .................................. 0613928.1

(51) Int. Cl.
*C07D 213/00* (2006.01)
*A61K 31/44* (2006.01)

(52) U.S. Cl. ........................................ 546/308; 514/352
(58) Field of Classification Search ........................ None
See application file for complete search history.

(56) References Cited

FOREIGN PATENT DOCUMENTS

| DE | 31 33 519 | 6/1982 |
|----|-----------|--------|
| DE | 197 16 984 | 10/1998 |
| EP | 0 977 736 | 9/2003 |

OTHER PUBLICATIONS

Schwoch, S. et al. "2,3-Dihydrospiro[1H-4-and 5-Azabenzimiadazole-2.1'-Cyclohexane] (=Spiro[cyclohexane-1,2'(3'H)-1'H-Imidazo[4, 5-b]pyridine) and Spiro[cyclohexane-1,2'(3'H)-1'H-Imidazo[4, 5-c]pyridine): Reactions with Nucleophiles" Helvetica Chimica Acta, vol. 77, No. 8, p. 2175-2190, (1994).
Landgraf, K.F. et al. "Polymorphism and desolvation of flupirtine maleate", European Journal of Pharmaceutics and Biopharmaceutics, vol. 46, p. 329-337, (1998).
Kuhnert-Brandst, M. et al "Contribution to Polymorphism of Drugs 7th Communication: Famotidine, Flupirtine Maleate, GYKI-51189, Paxamate, Propentofylline, and Triclabendazole" Scientia Pharmaceutica, vol. 58, p. 55-67, (1990), abstract only.
Caira, M.R. "Crystalline Polymorphism of Organic Compounds", Topics in Current Chemistry, vol. 198, p. 163-208, (1998).

*Primary Examiner* — Janet L. Andres
*Assistant Examiner* — Heidi Reese
(74) *Attorney, Agent, or Firm* — Merchant & Gould PC

(57) ABSTRACT

The present invention is concerned with new polymorphic forms of flupirtine maleate, processes for preparing the new polymorphic forms, pharmaceutical compositions containing them, therapeutic uses thereof and methods of treatment employing them.

3 Claims, 10 Drawing Sheets

PHARMACEUTICALLY ACCEPTABLE SALT AND POLYMORPHIC FORMS OF FLUPIRTINE MALEATE

Figure 1:
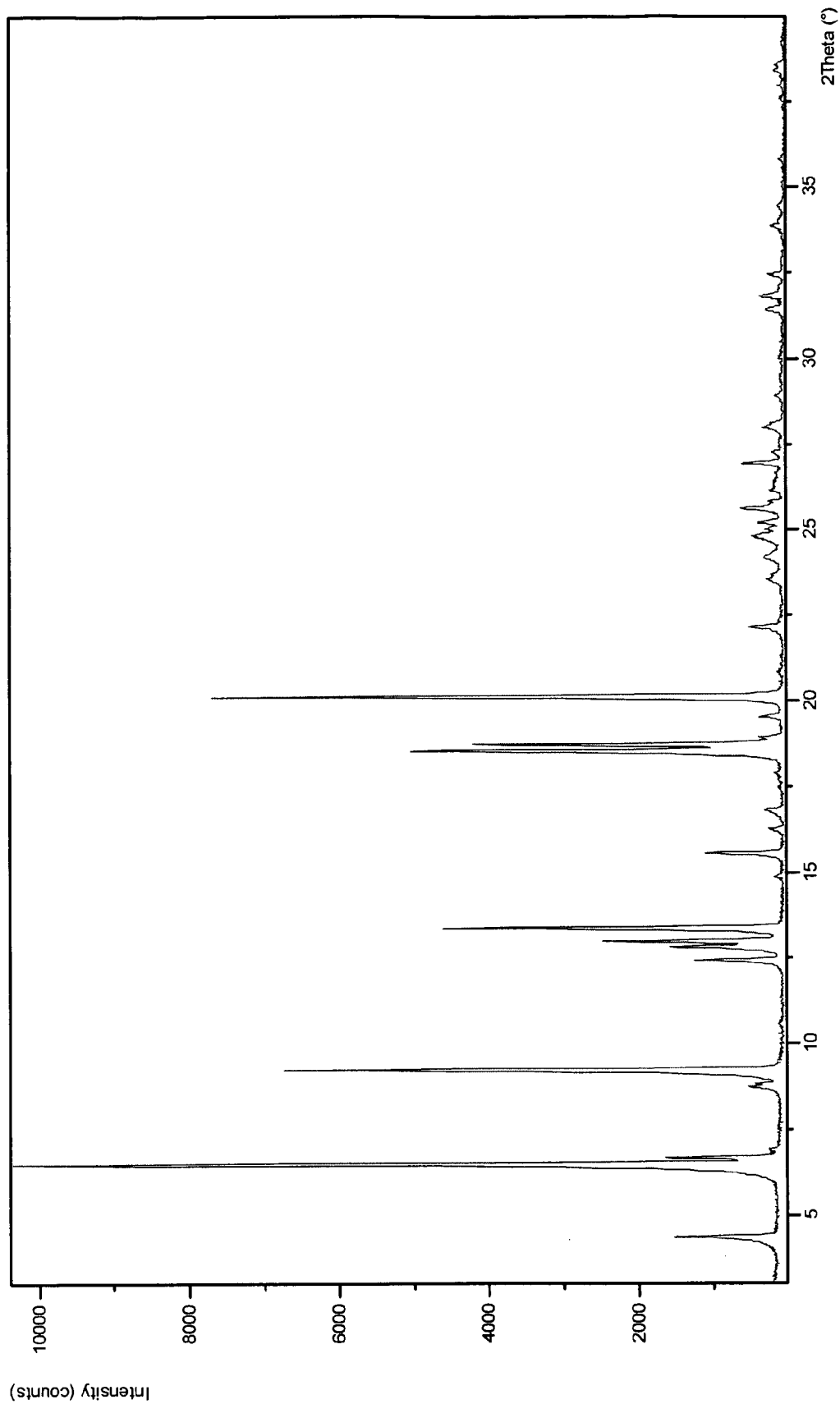

The present invention is concerned with new polymorphic forms of flupirtine maleate, processes for preparing the new polymorphic forms, pharmaceutical compositions containing them, therapeutic uses thereof and methods of treatment employing them.

Flupirtine maleate is chemically designated 2-amino-3-carbethoxyamino-6,4-fluorobenzylamino-pyridine maleate and can be represented by the following structural formula:

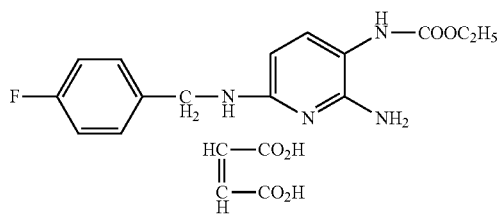

Flupirtine is a centrally acting non-opioid analgesic which is devoid of the typical side effects of natural or synthetic opioids, such as respiratory depression, constipation, tolerance, physical and/or psychological dependence and liability to cause addiction. It is also a muscle-relaxant. Although flupirtine does not appear to bind to any of the as yet identified. NMDA receptor complex associated binding sites, it has several functional NMDA antagonistic properties. Flupirtine has also been shown to increase the expression of the protein Bcl-2, which is known to inhibit apoptosis (programmed cell death).

As a result of these many and varied activities, flupirtine has a unique spectrum of pharmacological activity. Flupirtine has utility in the treatment and prevention of acute and chronic pain including neuropathic pain, nerve pain, cancer pain, vasomotor and migraine headaches, post-operative pain, post-traumatic pain, burn pain, erosion pain, dysmenorrhea, dental pain and the pain associated with degenerative and inflammatory joint disease.

Flupirtine also has utility in the treatment and prevention of muscular tension, muscle spasm and muscle stiffness. It is particularly useful in the treatment of back pain.

Additionally, flupirtine also exerts potent cyto- and neuro-protective effects and has utility in the treatment and prevention of neurodegenerative disorders such as Parkinson's disease, dementia including Alzheimer's disease, Huntington's chorea, multiple sclerosis, amyotrophic lateral sclerosis, encephalopathy including AIDS related encephalopathy, Creutzfeldt-Jakob disease including classical and new-variant types and Batten disease.

Flupirtine also has utility in the treatment and prevention of diseases of the eye such as maculopathy including senile macular degeneration, diabetic retinopathy, glaucoma and retinitis pigmentosa.

Flupirtine also has utility in the treatment and prevention of myocardial ischaemia and infarction, cerebral ischaemia and infarction, shock, tinnitus and hepatitis.

Flupirtine maleate is available under the trade mark Katadolon™.

EP 0 977 736 describes a process for preparing pure flupirtine maleate in crystalline form A. European Journal of Pharmaceutics and Biopharmaceutics 46 (1998) 329-337 describes crystallizates of flupirtine maleate obtained from isopropanol—these were designated as forms A and B and an isopropanol solvate form is also described, XRPD, polarization microscopy and thermoanalysis data is presented. In Scientia Pharmaceutica (Sci. Pharm.) 58, 55-67 (1990) is presented differential scanning calorimetry and IR spectra data for two forms of flupirtine maleate—which they designate as Modification I and Modification II. Modification I is said to have a m.p. of 170-178° C. and Modification II is said to have a m.p. of 154-162° C.

Polymorphic forms of a drug substance can have different chemical and physical properties, including melting point, chemical reactivity, solubility, dissolution rate, optical and mechanical properties, vapour pressure, and density. These properties can have a direct effect on the ability to process and/or manufacture a drug substance and a drug product, as well as on drug product stability, dissolution, and bioavailability. Thus, polymorphism can affect the quality, safety, and efficacy of a drug product.

Polymorphic forms as referred to herein can include crystalline and amorphous forms as well as solvate and hydrate forms, which can be further characterised as follows:

(i) Crystalline forms have different arrangements and/or conformations of the molecules in the Crystal lattice.

(ii) Amorphous forms consist of disordered arrangements of molecules that do not possess a distinguishable crystal lattice.

(iii) Solvates are crystal forms containing either stoichiometric or non-stoichiometric amounts of a solvent. If the incorporated solvent is water, the solvate is commonly known as a hydrate.

When a drug substance exists in polymorphic forms, it is said to exhibit polymorphism.

There are a number of methods that can be used to characterise polymorphs of a drug substance. Demonstration of a non-equivalent structure by single crystal X-ray diffraction is currently regarded as the definitive evidence of polymorphism. X-ray powder diffraction can also be used to support the existence of polymorphs. Other methods, including microscopy, thermal analysis (e.g., differential scanning calorimetry, thermal gravimetric analysis, and hot-stage microscopy), and spectroscopy (e.g., infrared (IR) and near infrared (NIR), Raman and solid-state nuclear magnetic resonance [ssNMR]) are also helpful to further characterise polymorphic forms.

Drug substance polymorphic forms can exhibit different chemical, physical and mechanical properties as referred to above, including aqueous solubility and dissolution rate, hygroscopicity, particle shape, density, flowability, and compactability, which in turn may affect processing of the drug substance and/or manufacturing of the drug product. Polymorphs can also exhibit different stabilities. The most stable polymorphic form of a drug substance is often chosen during drug development based on the minimal potential for conversion to another polymorphic form and on its greater chemical stability. However, a meta-stable form can alternatively be chosen for various reasons, including better bioavailability.

There is now provided by the present invention, therefore, polymorphic forms of the pharmaceutically acceptable salt of flupirtine, flupirtine maleate, with advantageous properties.

We have now surprisingly found that certain polymorphic forms of flupirtine maleate exhibit beneficial properties and, in particular, provide advantages over commercially available flupirtine maleate. The advantages are selected from, depending upon the form, increased physical stability, improved dissolution, improved morphology, improved properties when formulated and improved properties during storage.

More particularly, there is provided by the present invention polymorphic forms V, W, X, Y and Z of flupirtine maleate.

The crystalline structure of polymorph V of flupirtine maleate according to the present invention is characterised as having an X-ray powder diffraction pattern, or substantially the same X-ray powder diffraction pattern, as is shown in FIG. 1.

Polymorph V of flupirtine maleate according to the present invention is further characterised as having characteristic X-ray powder diffraction peaks (2θ) selected from one or more of the following: 6.5±0.2°, 9.3±0.2°, 13.4±0.2°, 18.6±0.2° and 20.1±0.2°. Further X-ray powder diffraction peaks (2θ) associated with polymorph V of flupirtine maleate according to the present invention are selected from one or more of the following: 4.4±0.2°, 12.4±0.2°, 12.8±0.2°, 15.6±0.2° and 22.2±0.2°.

Figure 2:
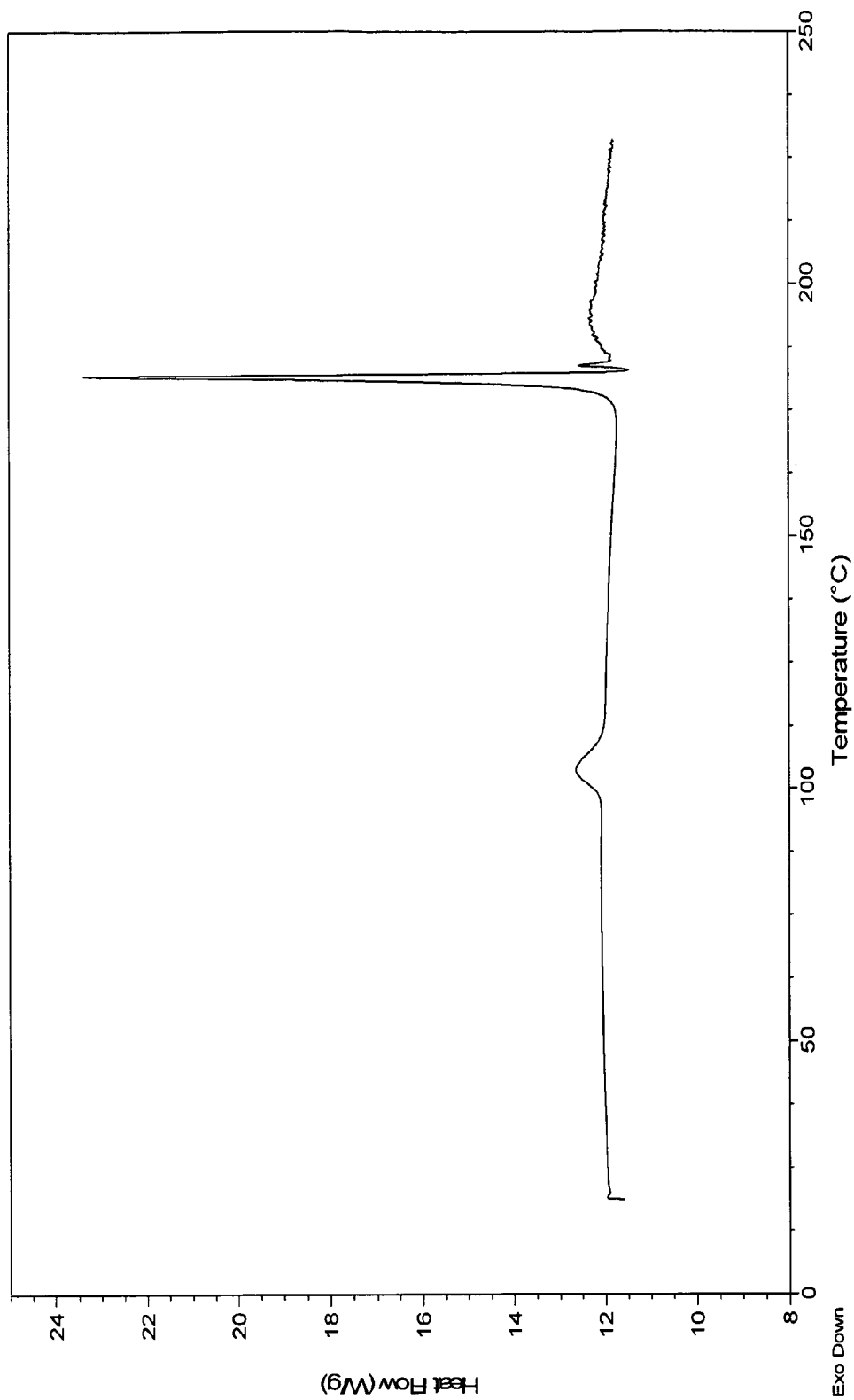

Polymorph V of flupirtine maleate according to the present invention is further characterised by a typical differential scanning calorimetry (DSC) thermogram as is shown in FIG. 2. Polymorph V of flupirtine maleate has a characteristic DSC endotherm in the range of 98-110° C. and in addition, has a melting endotherm of 180° C.±1° C.

Figure 3:
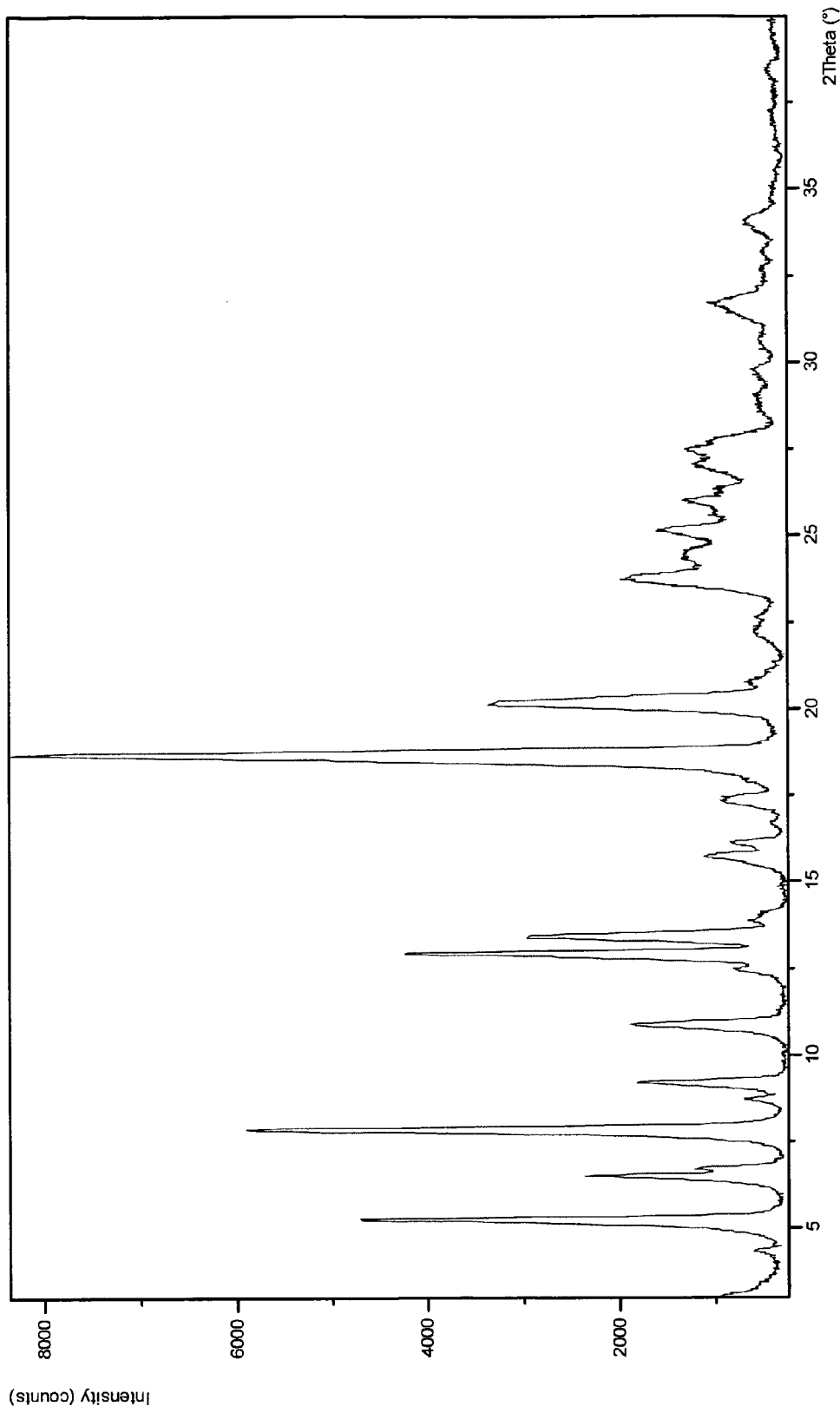

The crystalline structure of polymorph W of flupirtine maleate according to the present invention is characterised as having an X-ray powder diffraction pattern, or substantially the same X-ray powder diffraction pattern, as is shown in FIG. 3.

Polymorph W of flupirtine maleate according to the present invention is further characterised as having characteristic X-ray powder diffraction peaks (2θ) selected from one or more of the following: 5.3±0.2°, 7.9±0.2°, 13.0±0.2°, 18.7±0.2° and 20.1±0.2°. Further peaks (2θ) associated with polymorph W of flupirtine maleate according to the present invention are selected from one or more of the following: 6.5±0.2°, 9.2±0.2°, 10.9±0.2°, 13.4±0.2° and 15.8±0.2°.

Figure 4:
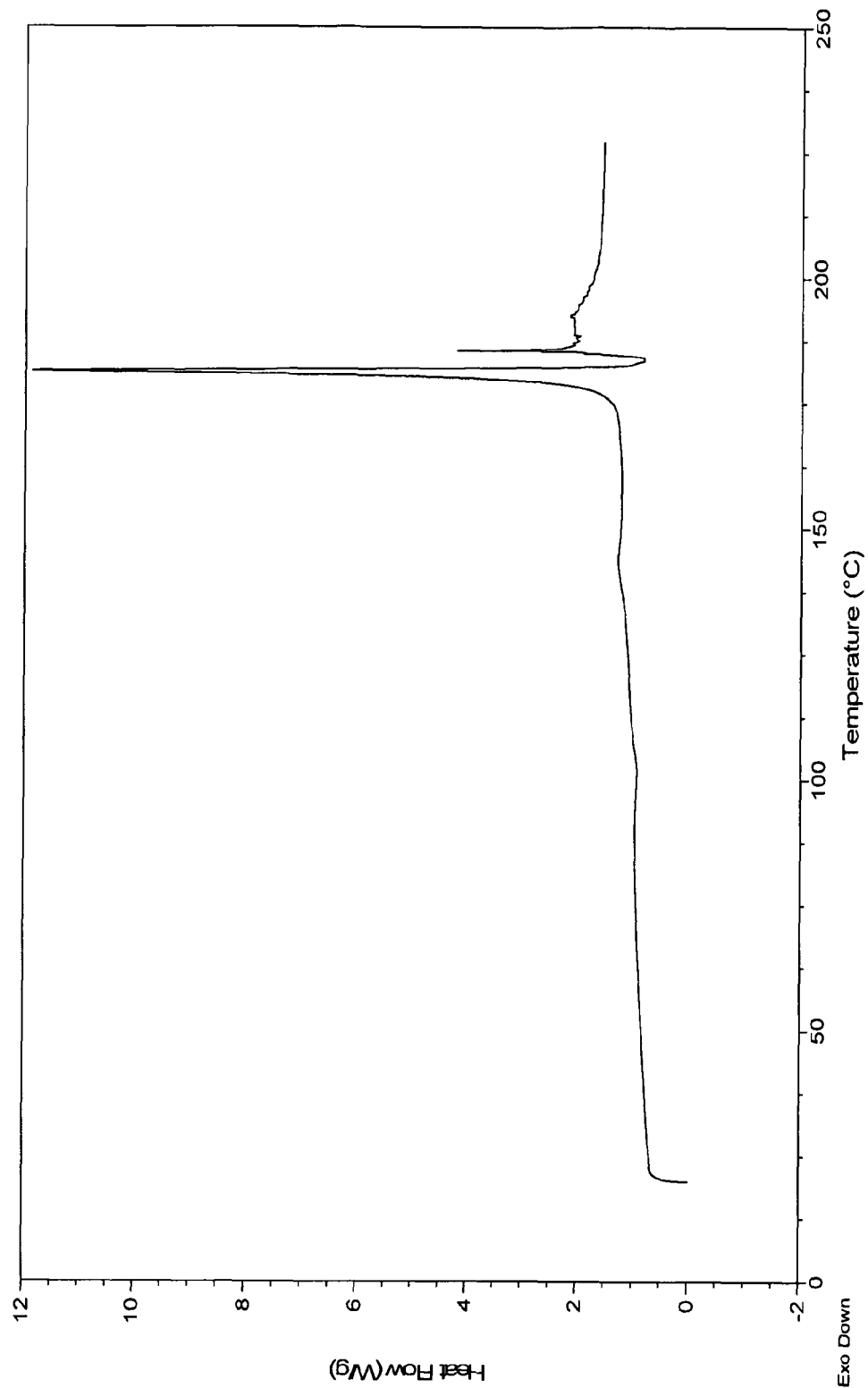

Polymorph W of flupirtine maleate according to the present invention is further characterised by a typical differential scanning calorimetry (DSC) thermogram as shown in FIG. 4. Polymorph W of flupirtine maleate has a characteristic melting endotherm at about 180° C.±1° C.

Figure 5:
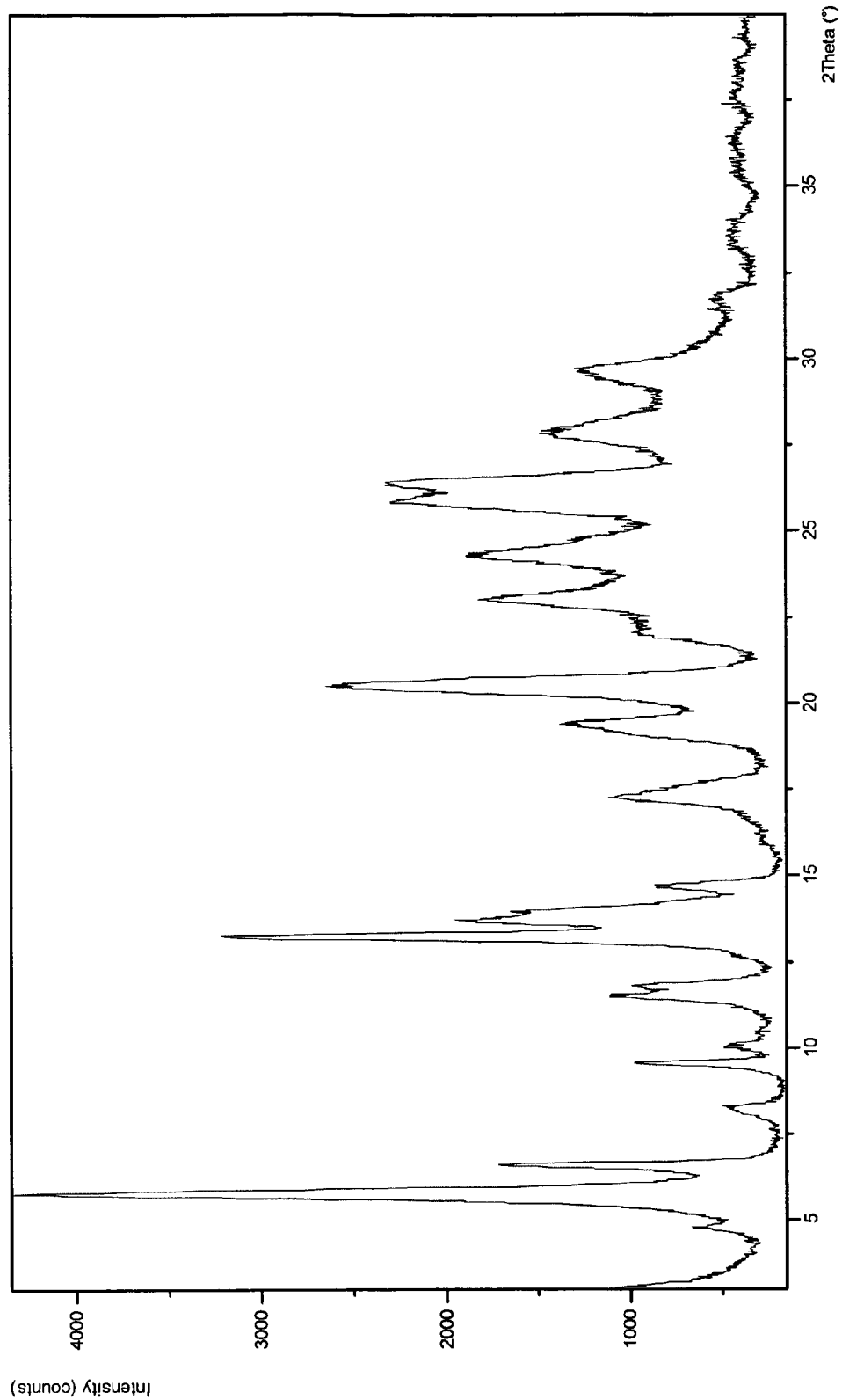

The crystalline structure of polymorph X of flupirtine maleate according to the present invention is characterised as having an X-ray powder diffraction pattern, or substantially the same X-ray powder diffraction pattern, as is shown in FIG. 5.

Polymorph X of flupirtine maleate according to the present invention is further characterised as having characteristic X-ray powder diffraction peaks (2θ) selected from one or more of the following: 5.8±0.2°, 13.3±0.2°, 19.4±0.2°, 20.6±0.2° and 24.2±0.2°. Further peaks (2θ) associated with polymorph X of flupirtine maleate according to the present invention are selected from one or more of the following: 6.6±0.2°, 17.3±0.2°, 23.0±0.2°, 24.2±0.2° and 26.5±0.2°.

Figure 6:
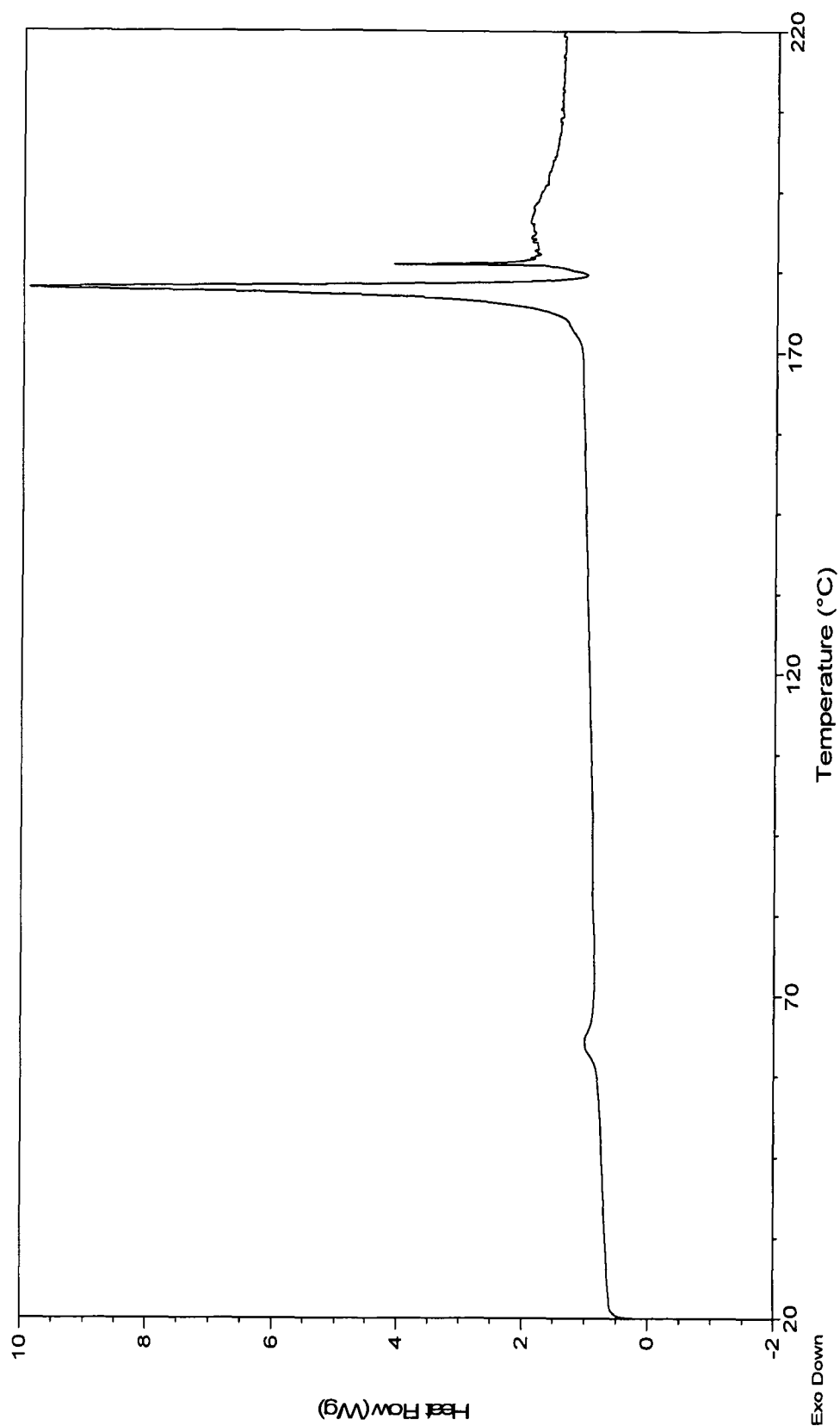

Polymorph X of flupirtine maleate according to the present invention is further characterised by a typical differential scanning calorimetry (DSC) thermogram as is shown in FIG. 6. Polymorph X of flupirtine maleate has a characteristic DSC enotherm in the range of 50-75° C. and, in addition, a melting endotherm at 179° C.±1° C.

Figure 7:
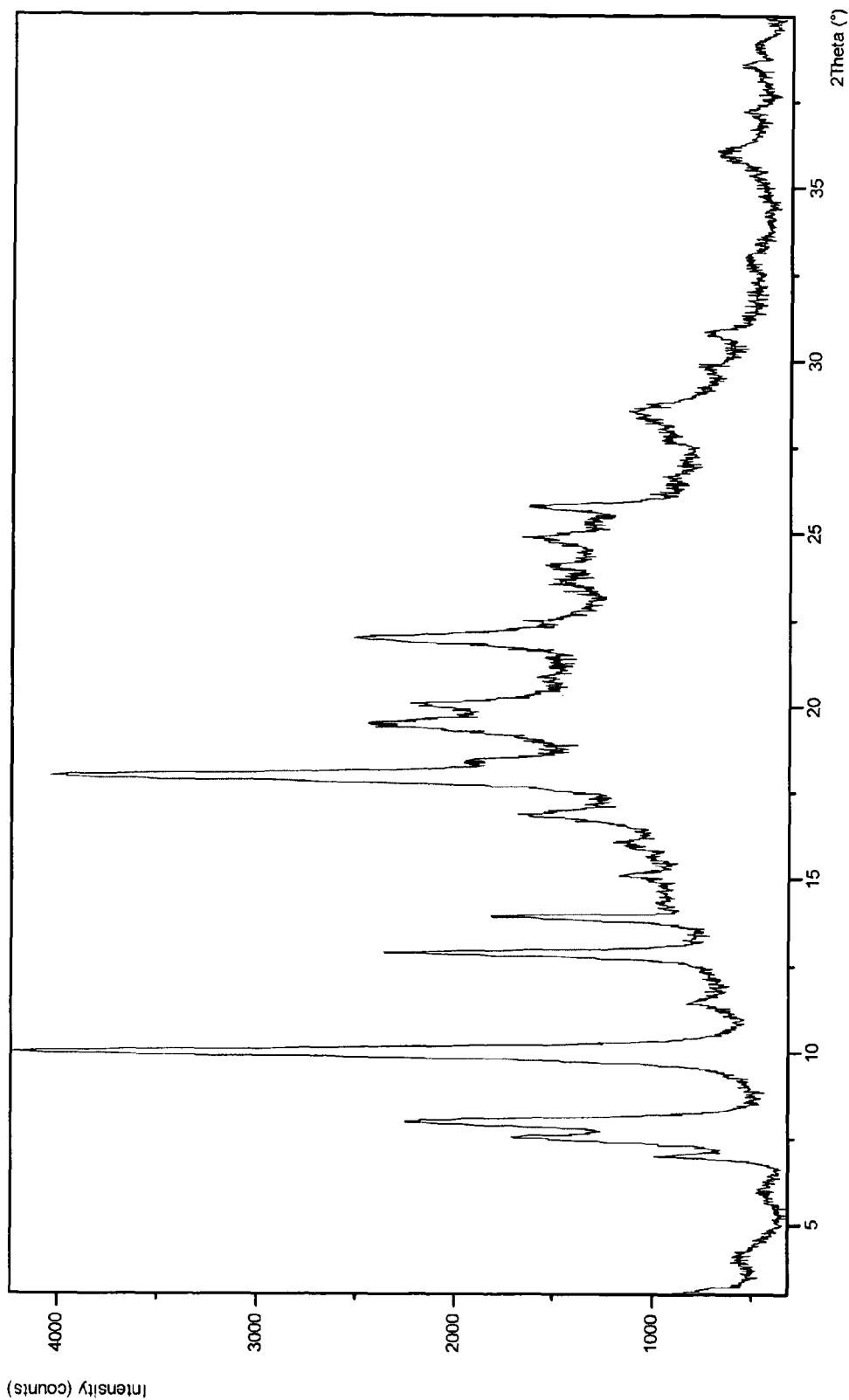

The crystalline structure of polymorph Y of flupirtine maleate according to the present invention is characterised as having an X-ray powder diffraction pattern, or substantially the same X-ray powder diffraction pattern, as is shown in FIG. 7.

Polymorph Y of flupirtine maleate according to the present invention is further characterised as having characteristic X-ray powder diffraction peaks (2θ) selected from one or more of the following: 8.0±0.2°, 10.0±0.2°, 12.9±0.2°, 18.0±0.2° and 19.5±0.2°. Further X-ray powder diffraction peaks (2θ) associated with polymorph Y of flupirtine maleate according to the present invention are selected from one or more of the following: 7.0±0.2°, 7.5±0.2°, 13.9±0.2°, 16.8±0.2° and 25.8±0.2°.

Figure 8:
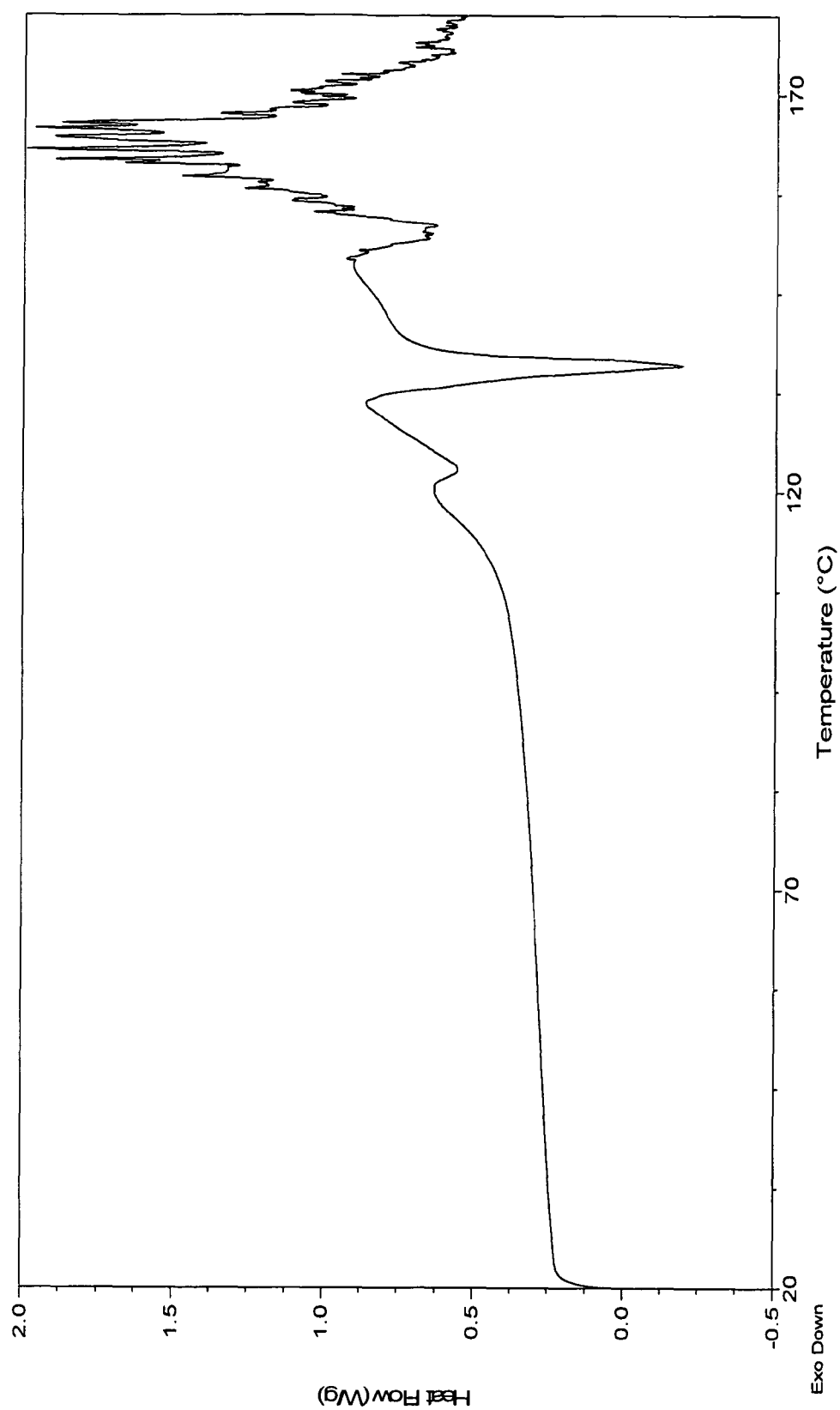

Polymorph Y of flupirtine maleate according to the present invention is further characterised by a typical differential scanning calorimetry (DSC) thermogram as shown in FIG. 8. Polymorph Y of flupirtine maleate has a characteristic DSC endotherm at 110° C.±1° C. and, in addition, at 119° C.±1° C. and, in addition, a characteristic exotherm at 134° C.±1° C. and, in addition, this is followed by degradation.

Figure 9:
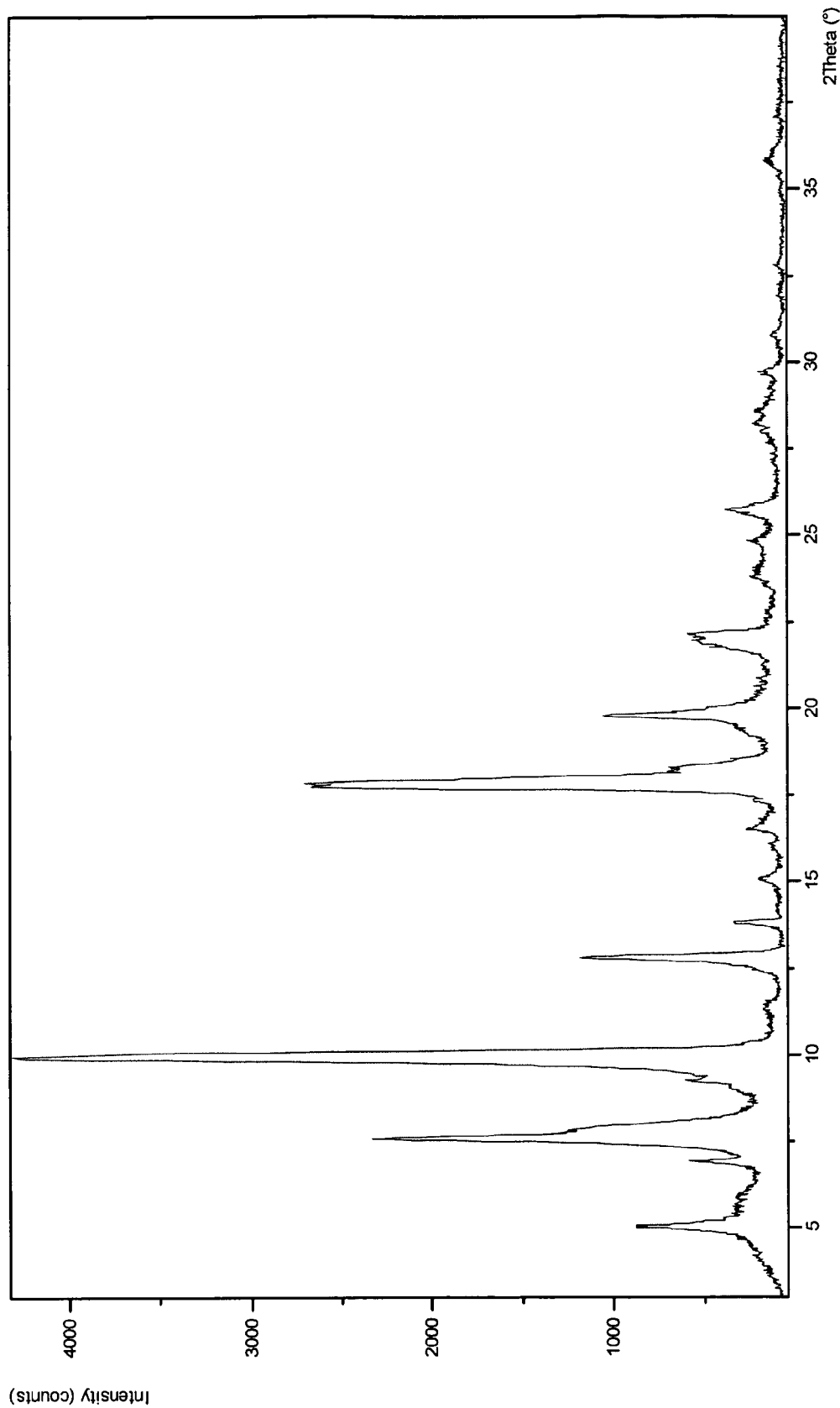

The crystalline structure of polymorph Z of flupirtine maleate according to the present invention is characterised as having an X-ray powder diffraction pattern, or substantially the same X-ray powder diffraction pattern, as is shown in FIG. 9. Polymorph Z of flupirtine maleate according to the present invention is further characterised as having characteristic X-ray powder diffraction peaks (2θ) selected from one or more of the following: 7.6±0.2°, 9.9±0.2°, 17.9±0.2° and 19.8±0.2°. Further peaks (2θ) associated with polymorph Z of flupirtine maleate according to the present invention are selected from one or more of the following: 5.1±0.2°, 6.9±0.2°, 12.8±0.2° and 22.2±0.2°.

Figure 10:
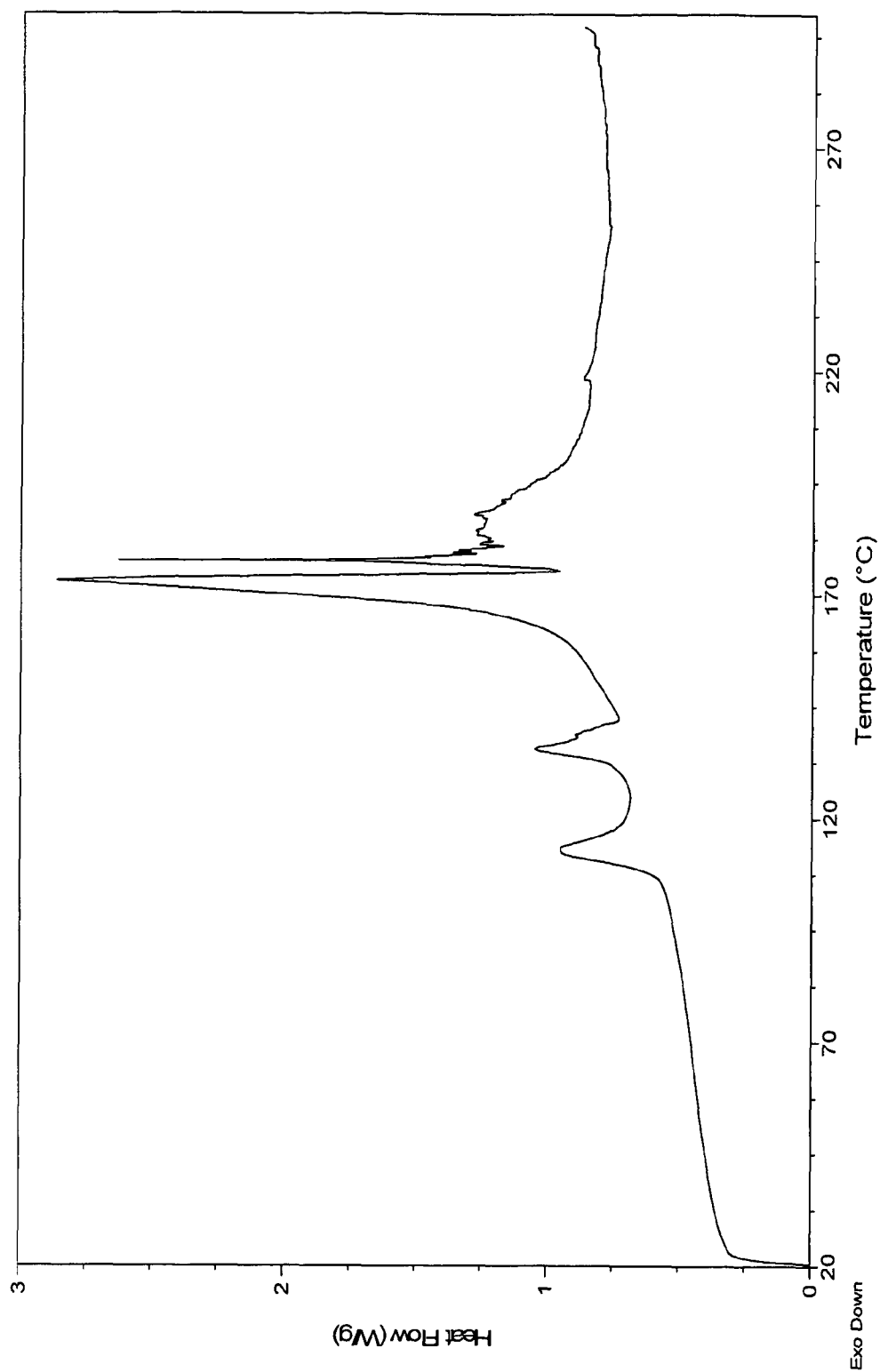

Polymorph Z of flupirtine maleate according to the present invention is further characterised by a typical differential scanning calorimetry (DSC) thermogram as shown in FIG. 10. Polymorph Z of flupirtine maleate has a characteristic DSC endotherm at 108° C.±1° C. and, in addition, a further DSC endotherm at 133° C.±1° C. and, in addition, a melting endotherm of 167° C.±1° C.

There is also provided by the present invention processes for preparing polymorphic forms of flupirtine maleate substantially as hereinbefore described.

In certain embodiments of a process as provided by the present invention a polymorphic form of flupirtine maleate substantially as hereinbefore described is formed by solvent crystallisation.

Polymorphic forms of flupirtine maleate, as provided by the present invention, are centrally acting non-opioid analgesics which are devoid of the typical side effects of natural or synthetic opioids, such as respiratory depression, constipation, tolerance, physical and/or psychological dependence and liability to cause addiction. They are also muscle-relaxants. They have functional NMDA antagonistic properties. They also increase the expression of the protein Bcl-2, which is known to inhibit apoptosis.

As a result of these many and varied activities, the polymorphic forms of flupirtine maleate, as provided by the present invention, have a unique spectrum of pharmacological activity. They have utility in the treatment and prevention of acute and chronic pain including neuropathic pain, nerve pain, cancer pain, vasomotor and migraine headaches, postoperative pain, post-traumatic pain, burn pain, erosion pain, dysmenorrhea, dental pain and the pain associated with degenerative and inflammatory joint disease.

They also have utility in the treatment and prevention of muscular tension, muscle spasm and muscle stiffness. They are particularly useful in the treatment of back pain.

Additionally, the polymorphic forms of flupirtine maleate, as provided by the present invention, exert potent cyto- and neuroprotective effects and have utility in the treatment and prevention of neurodegenerative disorders such as Parkinson's disease, dementia including Alzheimer's disease, Huntington's chorea, multiple sclerosis, amyotrophic lateral sclerosis, encephalopathy including AIDS related encephalopathy, Creutzfeldt-Jakob disease including classical and new-variant types and Batten disease.

They also have utility in the treatment and prevention of diseases of the eye such as maculopathy including senile macular degeneration, diabetic retinopathy, glaucoma and retinitis pigmentosa.

They also have utility in the treatment and prevention of myocardial ischaemia and infarction, cerebral ischaemia and infarction, shock, tinnitus and hepatitis.

The present invention further provides, therefore, pharmaceutical compositions comprising a therapeutically effective dose of a polymorphic form of flupirtine maleate according to the invention, together with a pharmaceutically acceptable cattier, diluent or excipient therefor. Excipients are chosen according to the pharmaceutical form and the desired mode of administration.

As used herein, the term "therapeutically effective amount" means an amount of a polymorphic form of flupirtine maleate according to the invention, which is capable of preventing, ameliorating or eliminating a disease state for which administration of a centrally acting non-opioid analgesics, a muscle-relaxant, a functional NMDA antagonist or a substance that increases the expression of the protein Bcl-2 is indicated.

By "pharmaceutically acceptable" it is meant that the carrier, diluent or excipient is compatible with a polymorphic form of flupirtine maleate according to the invention, and not deleterious to a recipient thereof.

In the pharmaceutical compositions of the present invention for oral, sublingual, subcutaneous, intramuscular, intravenous, topical, intratracheal, intranasal, transdermal or rectal administration, a polymorphic form of flupirtine maleate according to the present invention is administered to animals and humans in unit forms of administration, mixed with conventional pharmaceutical carriers, for the prophylaxis or treatment of the above disorders or diseases. The appropriate unit forms of administration include forms for oral administration, such as tablets, gelatin capsules, powders, granules and solutions or suspensions to be taken orally, forms for sublingual, buccal, intratracheal or intranasal administration, forms for subcutaneous, intramuscular or intravenous administration and forms for rectal administration. For topical application, a polymorphic form of flupirtine maleate according to the present invention can be used in creams, ointments or lotions. Oral administration is preferred.

To achieve the desired prophylactic or therapeutic effect, the dose of a polymorphic form of flupirtine maleate according to the present invention can vary between 0.01 and 50 mg per kg of body weight per day. Each unit dose can contain from 0.1 to 1000 mg, preferably 1 to 500 mg, of a polymorphic form of flupirtine maleate according to the present invention in combination with a pharmaceutical carrier. This unit dose can be administered 1 to 5 times a day so as to administer a daily dosage of 0.5 to 5000 mg, preferably 1 to 2500 mg.

When a solid composition in the form of tablets is prepared, a polymorphic form of flupirtine maleate according to the present invention is mixed with a pharmaceutical vehicle such as gelatin, starch, lactose, magnesium stearate, talc, gum arabic or the like. The tablets can be coated with sucrose, a cellulose derivative or other appropriate substances, or else they can be treated so as to have a prolonged or delayed activity and so as to release a predetermined amount of active principle continuously.

A preparation in the form of gelatin capsules can be obtained by mixing a polymorphic form of flupirtine maleate according to the present invention with a diluent and pouring the resulting mixture into soft or hard gelatin capsules.

A preparation in the form of a syrup or elixir or for administration in the form of drops can contain a polymorphic form of flupirtine maleate according to the present invention typically in conjunction with a sweetener, which is preferably calorie-free, optionally antiseptics such as methylparaben and propylparaben, as well as a flavouring agent and an appropriate colour.

Water-dispersible granules or powders can contain a polymorphic form of flupirtine maleate according to the present invention mixed with dispersants or wetting agents, or suspending agents such as polyvinylpyrrolidone, as well as with sweeteners or taste correctors.

Rectal administration is effected using suppositories prepared with binders which melt at the rectal temperature, for example polyethylene glycols.

Parenteral administration is effected using aqueous suspensions, isotonic saline solutions or sterile and injectable solutions which contain pharmacologically compatible dispersants and/or wetting agents, for example propylene glycol or butylene glycol.

A polymorphic form of flupirtine maleate according to the present invention can also be formulated as microcapsules, with one or more carriers or additives if appropriate.

There is also provided by the present invention a polymorphic form of flupirtine maleate substantially as hereinbefore described for use in therapy.

The present invention further provides a polymorphic form of flupirtine maleate substantially as hereinbefore described, for use in the manufacture of a medicament for the treatment of a disease state prevented, ameliorated or eliminated by the administration of a centrally acting non-opioid analgesic, a muscle-relaxant, a functional NMDA antagonist and/or an apoptosis inhibitor. More specifically, the present invention provides a polymorphic form of flupirtine maleate, substantially as hereinbefore described, for use in the manufacture of a medicament for treating and preventing a number of disorders including acute and chronic pain, including neuropathic pain, nerve pain, cancer pain, vasomotor and migraine headaches, post-operative pain, post-traumatic pain, burn pain, erosion pain, dysmenorrhea, dental pain, the pain associated with degenerative and inflammatory joint disease, muscular tension, muscle spasm, muscle stiffness, back pain, neurodegenerative disorders such as Parkinson's disease, dementia including Alzheimer's disease, Huntington's chorea, multiple sclerosis, amyotrophic lateral sclerosis, encephalopathy including AIDS related encephalopathy, Creutzfeldt-Jakob disease including classical and new-variant, Batten disease, diseases of the eye such as maculopathy including senile macular degeneration, diabetic retinopathy, glaucoma, retinitis pigmentosa, myocardial ischaemia and infarction, cerebral ischaemia and infarction, shock, tinnitus and hepatitis.

The present invention also provides a method of treating a disease state prevented, ameliorated or eliminated by the administration of a centrally acting non-opioid analgesic, a muscle-relaxant, a functional NMDA antagonist and/or an apoptosis inhibitor in a patient in need of such treatment, which method comprises administering to the patient a therapeutically effective amount of a polymorphic form of flupirtine maleate, substantially as hereinbefore described. More specifically, the present invention provides a method of treating a number of disorders, including acute and chronic pain, including neuropathic pain, nerve pain, cancer pain, vasomotor and migraine headaches, post-operative pain, post-traumatic pain, burn pain, erosion pain, dysmenorrhea, dental pain, the pain associated with degenerative and inflammatory joint disease, muscular tension, muscle spasm, muscle stiffness, back pain, neurodegenerative disorders such as Parkinson's disease, dementia including Alzheimer's disease, Huntington's chorea, multiple sclerosis, amyotrophic lateral sclerosis, encephalopathy including AIDS related encephalopathy, Creutzfeldt-Jakob disease including classical and new-variant, Batten disease, diseases of the eye such as maculopathy including senile macular degeneration, diabetic retinopathy, glaucoma, retinitis pigmentosa, myocardial ischaemia and infarction, cerebral ischaemia and infarction, shock, tinnitus and hepatitis, in a patient in need of such treatment, which method comprises administering to the patient a therapeutically effective amount of a polymorphic form of flupirtine maleate, substantially as hereinbefore described.

There is also provided by the present invention a polymorphic form of flupirtine maleate, substantially as hereinbefore described, for use in the manufacture of a medicament for the treatment of a disease state prevented, ameliorated or eliminated by the administration of a centrally acting non-opioid analgesic, a muscle-relaxant, a functional NMDA antagonist and/or an apoptosis inhibitor, wherein the polymorphic form of flupirtine maleate according to the invention, provides an enhanced therapeutic effect compared to the therapeutic effect provided by the existing polymorphic forms of flupirtine maleate. The present invention also provides a corresponding method of treatment, which comprises administering to a patient a therapeutically effective amount of a polymorphic form of flupirtine maleate, substantially as hereinbefore described, so that the administered polymorphic form of flupirtine maleate according to the present invention, provides an enhanced therapeutic effect to the patient, compared to the therapeutic effect provided by corresponding administration of the existing polymorphic forms of flupirtine maleate.

The present invention can be further illustrated by the following Figures and non-limiting Examples.

With reference to the Figures, these are as follows:

FIG. 1: X-ray powder diffraction pattern of flupirtine maleate polymorph V according to the present invention obtained by using a Philips X'Pert PRO with CuKα radiation in 2θ=3-40° range FIG. 2: Differential Scanning calorimetry (DSC) thermogram of flupirtine maleate polymorph V obtained by using a DSC Pyris 1 manufactured by Perkin-Elmer. The experiment was done under a flow of nitrogen (35 ml/rain) and heating rate was 10° C./min. A standard sample pan was used.

FIG. 3: X-ray powder diffraction pattern of flupirtine maleate polymorph W according to the present invention obtained by using a Philips X'Pert PRO with CuKα radiation in 2θ=3-40° range.

FIG. 4: Differential Scanning calorimetry (DSC) thermogram of flupirtine maleate polymorph W obtained by using a DSC Pyris 1 manufactured by Perkin-Elmer. The experiment was done under a flow of nitrogen (35 ml/min) and heating rate was 10° C./min. A standard sample pan was used.

FIG. 5: X-ray powder diffraction pattern of flupirtine maleate polymorph X according to the present invention obtained by using a Philips X'Pert PRO with CuKα radiation in 2θ=3-40° range.

FIG. 6: Differential Scanning calorimetry (DSC) thermogram of flupirtine maleate polymorph X obtained by using a DSC Pyris 1 manufactured by Perkin-Elmer. The experiment was done under a flow of nitrogen (35 ml/min) and heating rate was 10° C./min. A standard sample pan was used.

FIG. 7: X-ray powder diffraction pattern of flupirtine maleate polymorph Y according to the present invention obtained by using a Philips X'Pert PRO with CuKα radiation in 2θ=3-40° range.

FIG. 8: Differential Scanning calorimetry (DSC) thermogram of flupirtine maleate polymorph Y obtained by using a DSC Pyris 1 manufactured by Perkin-Elmer. The experiment was done under a flow of nitrogen (35 ml/min) and heating rate was 10° C./min. A standard sample pan was used.

FIG. 9: X-ray powder diffraction pattern of flupirtine maleate polymorph Z according to the present invention obtained by using a Philips X'Pert PRO with CuKα radiation in 2θ=3-40° range.

FIG. 10: Differential Scanning calorimetry (DSC) thermogram of flupirtine maleate polymorph Z obtained by using a DSC Pyris 1 manufactured by Perkin-Elmer. The experiment was done under a flow of nitrogen (35 ml/min) and heating rate was 10° C./min. A standard sample pan was used.

Flupurtine Maleate can be synthesised in accordance with the processes described in the literature, such as US595115, WO0139760 and WO9505175.

The following examples are for the purpose of illustration of the invention only and are not intended in any way to limit the scope of the present invention. It will thus be readily apparent to one skilled in the art that varying substitutions and modifications may be made to the invention disclosed herein without departing from the scope and spirit of the invention. Thus, it should be understood that although the present invention has been specifically disclosed by preferred embodiments and optional features, modification and variation of the concepts herein disclosed may be resorted to by those skilled in the art, and that such modifications and variations are considered to be falling within the scope of the invention.

EXAMPLES

Example 1

Preparation of Flupirtine Maleate Form V 250 mg of flupirtine maleate was dissolved in 35 mL of methyl acetate whilst heating. Hot solution was filtered and crystallisation of needle like crystals occurred while cooling the solution to room temperature. The product was collected by filtration and dried overnight at room temperature. 136 mg of a white crystalline product was obtained.

Example 2

Preparation of Flupirtine Maleate Form W 500 mg of flupirtine maleate was placed in 3-neck round bottom flask filled with a mixture of 96% ethanol (15 mL) and dichloromethane (30 mL). The reaction mixture was refluxed for 20 minutes whilst stirring and then cooled in an ice bath to room temperature. Stirring was then continued at room temperature overnight. The product was filtered and dried overnight at room temperature. 314 mg of a white product was obtained.

Example 3

Preparation of Flupirtine Maleate Form X 500 mg of flupirtine maleate was dissolved in 10 mL of 96% ethanol. The solution was heated and the hot solution was filtered and added dropwise to 20 mL of hot methyl acetate. The mixture was stirred at room temperature and precipitation of a crystalline product occurred. The product was filtered. 320 mg of a white product was obtained.

Example 4

Preparation of Flupirtine Maleate Form Y 500 mg of flupirtine maleate was placed in 3-neck round bottom flask filled with a mixture of 96% ethanol (15 mL) and methyl benzoate (30 mL). The reaction mixture was refluxed for 20 minutes whilst stirring and then slowly cooled to room temperature. Stirring was continued at room temperature and after 3 hours crystallisation occurred. The reaction mixture was stirred for an additional 3 hours. A white product was obtained. The product was filtered and dried overnight at room temperature. 436 mg of a white product was obtained.

Example 5

Preparation of Flupirtine Maleate Form Z 50 mg of flupirtine maleate was dissolved in 2 mL of anhydrous methyl benzoate whilst heating. The resulting solution was placed in a closed bottle to crystallise at room temperature. The product was filtered and dried over night at room temperature. 32 mg of a white crystalline product was obtained.

XRPD analysis was carried out on Philips X'Pert PRO diffractometer using CuKα1 radiation Experimental Conditions:

| | |
|---|---|
| Sample holder preparation | Samples after being powdered in a mortar and pestle are applied directly on silicon PW1817/32 "zero background" holder |
| Instrument | Philips X'Pert PRO |
| Goniometer | PW3050/60 |
| Generator | PW3040; 45 kV, 40 mA |
| X-Ray tube | PW3373/00; Cu anode LFF |
| Focus | Linear |
| Sample stage | PW3072/60 or PW3064 |
| Scan angle range (2Θ) | 4-40° |
| Scan mode | Continuous absolute scan |
| Step size (2Θ) | 0.016° |
| Time per step | 100 seconds |
| X-ray radiation | $\lambda(CuK\alpha_1)$ = 1.540598 Å |
| Primary soller slit | 0.04 rad |
| PDS | Fixed, divergence ½° |
| Primary mask | 10 mm |
| Secondary soller slit | 0.04 rad |
| Monochromator | Inc. Beam $\alpha_1$ Cu/Co for reflection mode |
| Detector | X'Celerator (2.022° 2Θ) |
| Control program | X'Pert Data Collector |
| Temperature | 293 ± 3 K |

The invention claimed is:

1. Polymorph X of flupirtine maleate characterized by data selected from the group consisting of:
   a) having an X-ray powder diffraction pattern, or substantially the same X-ray powder diffraction pattern, as shown in FIG. 5 and
   b) having characteristic X-ray powder diffraction peaks (2θ): 5.8±0.2°, 13.3±0.2°, 19.4±0.2°, 20.6±0.2° and 24.2±0.2°.

2. A polymorph according to claim 1, further characterised by X-ray powder diffraction peaks (2θ) selected from one or more of the following: 6.6±0.2°, 17.3±0.2°, 23.0±0.2°, 24.2±0.2° and 26.5±0.2°.

3. A method of treating a disease state prevented, ameliorated or eliminated by the administration of centrally acting non-opioid analgesics, muscle-relaxants, functional NMDA antagonists or substances that increase the expression of the protein Bcl-2, in a patient in need of such treatment, which comprises administering to the patient a therapeutically effective amount of a polymorphic form of flupirtine maleate according to claim 1.

* * * * *